US00PP09899P

United States Patent [19]

Plate

[11] Patent Number: Plant 9,899

[45] Date of Patent: May 20, 1997

[54] ANTHURIUM PLANT NAMED DOLLY

[75] Inventor: Renate Plate, Bremen, Germany

[73] Assignee: Wolfgang Bock Pflanzenexport KG, Bremen, Germany

[21] Appl. No.: 563,606

[22] Filed: Nov. 28, 1995

[51] Int. Cl.[6] ..... A01H 5/00

[52] U.S. Cl. ..... Plt./88.1

[58] Field of Search ..... Plt./88.1

[56] References Cited

U.S. PATENT DOCUMENTS

P.P. 5,696 3/1986 van der Laarse ..... Plt./88.1

P.P. 9,169 6/1995 Lamb et al. ..... Plt./88.1

*Primary Examiner*—James R. Feyrer

*Attorney, Agent, or Firm*—Foley & Lardner

[57] ABSTRACT

A new and distinct Anthurium plant named 'Dolly' particularly characterized by its large, round, thick, reflexed or cupped bright orange spathes with a contrasting yellow-orange spadix. The spathes are held straight above the foliage in the center of the plant. The leaves of Dolly are large, wide, stiff, leathery, moderately thick, with distinctive puckering along the midrib.

1 Drawing Sheet

The present invention comprises a new and distinct cultivar of Anthurium, botanically known as *Anthurium scherzerianum*, and referred to by the cultivar name 'Dolly'.

The new cultivar is a product of a breeding program carried out by the inventor Renate Plate in Bremen, Germany. The new cultivar Dolly is the result of a cross of selected but presently unknown parentage made by the inventor in Bremen, Germany. The new cultivar was discovered from the progeny of the stated cross by the inventor. Asexual propagation by tissue culture done under the supervision of the inventor in Bremen, Germany was used to increase the number of plants for evaluation and has demonstrated the stability of the combination of characteristics of the new cultivar from generation to generation.

The following observations, measurements and values describe plants grown in Apopka, Fla. under greenhouse conditions which closely approximate those generally used in horticultural practice.

The following traits have been repeatedly observed to be characteristics which is combination distinguish 'Dolly' from other *Anthurium scherzerianum* cultivars and from the patented cultivar 'Shazzam', disclosed in U.S. Plant Pat. No. 9,169.

1. Plants of 'Dolly' produce large, round, thick, bright orange spathes which are often reflexed or cupped, and puckered. The spadix is a contrasting yellow-orange. Plants of 'Shazzam', by comparison, produce more elliptical, red-orange spathes which are of thinner substance.

2. Unlike 'Shazzam', spathes of 'Dolly' are held above the foliage in the center of the plant on thick, sturdy orange peduncles.

3. The spathes of 'Dolly' are orange when newly open and lighten in color with age. The spadix becomes twisted with age.

4. The leaves of 'Dolly' are large, wide, stiff, leathery, moderately thick, with distinctive puckering of the leaf blade along the midrib. Leaves of 'Shazzam', by comparison, are smaller, thinner, and more flexible.

All color references are measured against The Royal Horticultural Society Color Chart. Colors are approximate as color depends on horticultural practices such as light level and fertilization rate, among others, without, however, any change in genotype.

The color photographic drawing comprises a top perspective view of the inflorescence and foliage of a plant of 'Dolly' in a 15.2 cm pot. The photograph was taken approximately 11 months after planting a 16 week old liner obtained by tissue culture and grown under appropriate growing conditions. Colors are as accurate as possible with color illustrations of this type.

Origin: Seedling of selected parentage.

Classification: *Anthurium scherzerianum*, cv. 'Dolly'.

Propagation: Asexual production by tissue culture.

Inflorescence

*Immature.*—The spathe is tightly rolled around the spadix and emerges from the petiole sheath. The spathe is fully open when the pedicel is fully elongated, approximately 18 cm to 22 cm above the soil surface. The color of the peduncle is greener than, but closest to 166 B, often becoming orange 41 A near the base of the spathe.

*Color.*—Immature: Upper surface: Glossy 43 A. Lower surface: Very glossy 43 A. Mature: Upper surface: Matte 44 C. Lower surface: Glossy 39 B.

*Arrangement.*—The spathes stand up straight on thick sturdy peduncles and open above the leaves at about the center of the plant.

*Shape.*—The spathe is round with a cordate base, with the lobes of the spathe often overlapping, and a cuspidate apex that is hooked or twisted. It is distinctly cupped when new and puckered, and often reflexed with age. The spathes are approximately 9.5 cm to 11.2 cm in length, approximately 10.5 cm to 13 cm in width, and approximately 2.5 cm in depth if cupped. The spathes are equally as likely to reflex and become cupped outwardly.

*Flowering time.*—After approximately 11 months from a 16 week old liner from an untreated plant having three growing points as illustrated in the photograph, and depending on season, approximately 3 to 5 inflorescenses will be present. First flowers (2 to 3) can be expected approximately 4 months after planting a 16 week old liner.

Reproductive organs:

*Spadix.*—Size: Approximately 7.0 cm to 8.2 cm in length and approximately 8 mm in width. The spadix is straight when the spathe first unrolls, but quickly becomes twisted as the spathe opens fully. Color:

The spadix is 32 A, 33 A when new, and 26 A when fully emerged. Stamens: Anthers and filaments are minute, and not clearly visible. Pollen: 158 D in color. Pistil: Translucent 19 C in color, protruding between the staminate flowers, firmly fixed to the main axil. The pistilate flowers extend approximately 0.5 mm beyond the staminate flowers.

General appearance: Under appropriate growing conditions, Dolly attains a mature size of approximately 18.5 cm to 20 cm in height and approximately 45 cm to 49 wcm in width.

Leaves:

*Form.*—The leaf blade is broadly ovate with a cuspidate to acute apex and a cordate base. The margins are entire. The midrib is straight over the length of the leaf. The leaf blade is distinctly puckered, and folded upward from the midrib. The leaf margin is generally straight, but often curved downward. The upper leaf surface is slightly glossy, more so on newly emerged leaves. The leaves are stiff, leathery, and moderately thick.

*Size.*—Leaf blades of a mature sized plant are approximately 18 cm to 22.0 cm in length and approximately 18 cm to 22.0 cm in length and approximately 10.5 cm to 12.5 cm in width.

*Veins.*—Veins are sunken, and the leaf blade is often distinctly puckered or concave between veins. The midrib protrudes from the upper surface of the leaf for the length of the leaf. Primary veins border the perimeter of the leaf.

*Petiole.*—The petiole is approximately 9.8 cm to 12.5 cm in height from the base of the petiole to the base of the leaf blade. The petiole is approximately 4.0 mm in diameter just below the geniculum, and straight. Two parallel ridges run the length of the upper surface of the petiole.

*Petiole wings.*—Petiole wings are approximately 2.0 cm to 2.8 cm in length and approximately 5.0 mm in width at their midpoint. The tips of the petiole wings taper to a rounded point. There is approximately 7.9 cm to 9.1 cm between the top of the wing and the base of the geniculum.

*Geniculum.*—The geniculum is approximately 10 mm in length and 7 mm in diameter. The color is 145A.

*Lobes.*—The leaf has two rounded lobes which extend past the petiole. The distance from the petiole/leaf juncture to the highest point on the lobes is approximately 3.0 cm.

*Color.*—Upper surface: 137 A. Lower surface: 146 C D. Midrib, upper surface: 146 B. Midrib, lower surface: 145 C, Petiole: 146 B C. Petiole Wing: 137 A.

Roots: Greenish fleshy roots with fine laterals. The roots are 187 A in color when located above the soil.

General observation: Anthurium 'Dolly' produces large, round, thick, puckered, reflexed or cupped bright orange spathes with a contrasting yellow-orange spadix. The inflorescenses are held straight above the leaves in the center of the plant on thick, sturdy orange peduncles. The leaves are large, wide, stiff, very leathery, with distinctive puckering along the midrib.

I claim:

1. A new and distinct cultivar of Anthurium plant named 'Dolly', as illustrated and described.

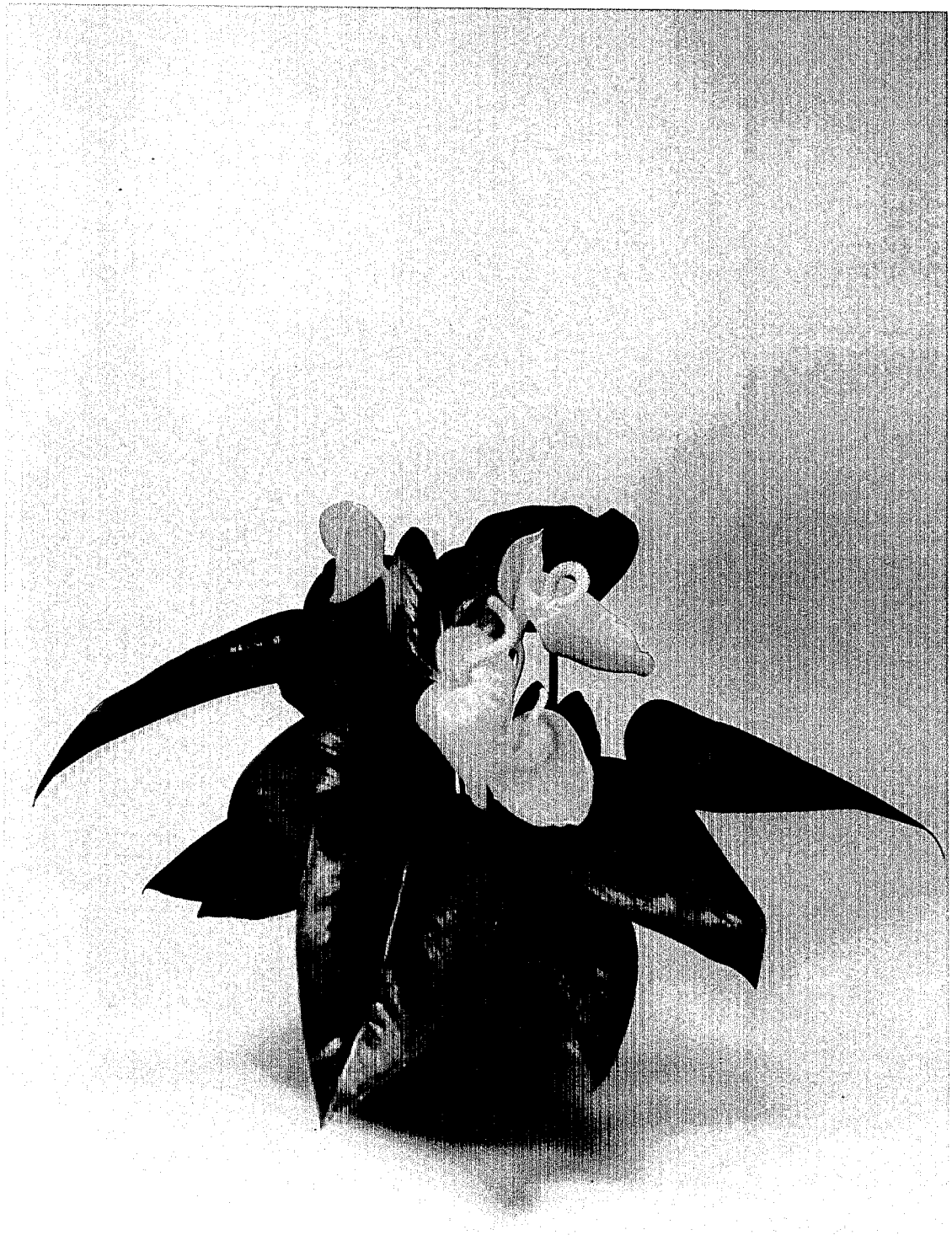

* * * * *